United States Patent [19]

Warriner

[11] Patent Number: Plant 6,255

[45] Date of Patent: Aug. 23, 1988

[54] ROSE PLANT JACRIM

[75] Inventor: William A. Warriner, Tustin, Calif.

[73] Assignee: Jackson & Perkins Company, Medford, Oreg.

[21] Appl. No.: 908,064

[22] Filed: Sep. 16, 1986

[51] Int. Cl.[4] ..... A01H 5/00

[52] U.S. Cl. ..... Plt./22

[58] Field of Search ..... Plt./22

*Primary Examiner*—Robert E. Bagwill

*Attorney, Agent, or Firm*—Majestic, Gallagher, Parsons & Siebert

[57] ABSTRACT

A floribunda rose variety having vigorous upright growth-producing medium length stems bearing unusually colored off-white fringed with red flowers, a high degree of mildew resistance and high quality foliage.

1 Drawing Sheet

This present invention relates to a new and distinct variety of rose plant of the floribunda class which was originated by crossing the variety Prominent, U.S. Plant Pat. No. 3,380, with an unnamed variety.

The primary objective of this breeding was to produce a new rose variety suitable for greenhouse cut flower production possessing better stem quality than "La Minuette". This objective was substantially achieved along with other desirable improvements as evidenced by the following unique combination of characteristics which are outstanding in the new variety and which distinguish it from its parents as well as from all other varieties of which I am aware:

1. A vigorous plant producing flowers on medium length stems;
2. An unusual color combination with white to off-white fringed with red;
3. Stiff petals;
4. Powdery mildew resistance;
5. Medium-sized leaves of excellent color; and
6. Short, somewhat thorny, peduncles.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color in terminology in accordance with The Royal Horticultural Society Colour Chart except where ordinary dictionary significance of color is indicated:

Parentage:

*Seed parent.*—Prominent, U.S. Plant Pat. No. 3,380.

*Pollen parent.*—Unnamed variety.

Classification:

*Botanical.*—Rosa hybrid.

*Commercial.*—Floribunda.

FLOWER

Observations made from specimens grown in a greenhouse at Irvine, Calif. in July, 1986.

Blooming habit: Continuous.

Bud:

*Size.*—1½" when petals start to unfurl.

*Form.*—Long, pointed.

*Color.*—When sepals first divide, Yellow-white Group 158C with each petal fringed with Red Group 45A to B; when half brown, upper side of petals Yellow-white Group 158C with each petal fringed with Red Group 45A and B; each petal has a small yellow base, Yellow Group 4B to C; lower side of petals White Group 158B with the upper rim edged in Red Group 45A and B.

*Sepals.*—Color: Green Group 138B. Three appendaged sepals normally appendaged. Two unappendaged sepals smooth edge.

*Receptacle.*—Color: Green Group 138B. Shape: Funnel. Size: Small. Surface: Smooth.

*Peduncle.*—Length: Short. Surface: Prickly. Color: Medium green. Strength: Stiff.

*Opening.*—Opens moderately fast in a spiral.

Open Bloom:

*Size.*—Medium. Average open size 3".

*Borne.*—Singly or several together.

*Stems.*—Medium, strong and wiry.

*Form.*—When first open, high center. Permanence: Flattens; outer petal edges slightly curled.

*Petalage.*—Number of petals under normal conditions: 28–30.

*Color.*—Center of flower: Upper side of petals, Petal edges dominated by Red Group 45B, petals then fade to a Red Pink (45D) to Near White (Yellow-White Group 158C; as the flower ages, the Yellow-White Group darkens to Yellow-Orange Group 15C. Reverse side of petals, Petal edges are Red Group 45B with the rest of the petal White Group 158B except near the base where it darkens to Yellow Group 4B to C. Base of petals, Yellow Group 4B to C. Major color: Red Group 45A and B.

*Discoloration.*—General tonality at end of first day: None. Third day: Some darkening of the Yellow-White Group 158C to a Yellow-Orange 15C.

*Fragrance.*—Slight.

Petals:

*Texture.*—Thick.

*Shape.*—Round, notched.

*Form.*—Tips slightly recurved.

*Arrangement.*—Imbricated.

*Persistence.*—Drop off cleanly.
*Lastingness.*—On the plant, fair. As cut flower, fair.

Reproductive parts:
*Anthers.*—Medium. Color: Yellow. Arrangement: Regular around styles.
*Filaments.*—Color: Yellow-Green.
*Pollen.*—Gold yellow.
*Styles.*—Color: Red.
*Stigmas.*—Color: White.

PLANT

Form: Bush.
Growth: Very vigorous, upright.
Foliage: Number of leaflets on normal mid-stem leaves: 5 with occasionally 7.
*Size.*—Medium.
*Quantity.*—Normal.
*Color.*—New foliage: Green 137A with an underlay of Red. Old foliage: Normal Green 137A with the underside somewhat lighter Green 136C.

Leaflets:
*Shape.*—Oval pointed.
*Texture.*—Smooth.
*Edge.*—Serrated.
*Serration.*—Single, small.

*Petiole.*—Rachis: Color: Reddish. Underside: Rough, with prickles.
*Stipules.*—Medium, bearded.
*Disease resistance.*—Resistant to mildew, under normal growing conditions at Irvine, Calif.

Wood:
*New wood.*—Color: Light green. Bark: Smooth.
*Old wood.*—Color: Green. Bark: Smooth.

Prickles:
*Quantity.*—On main canes from base: Ordinary. On laterals from main canes: Ordinary.
*Form.*—Medium, straight to slightly hooked downward.
*Color when young.*—Green.

Small prickles:
*Quantity.*—On main stalks, none. On laterals, few.
*Color.*—Green.

I claim:

1. A new and distinct variety of rose plant of the floribunda class, substantially as herein shown and described, characterized particularly as to novelty by the unique combination of its vigorous upright growth producing medium length stems bearing unusually colored off-white fringed with red flowers, its high degree of mildew resistance and its high quality foliage.

* * * * *

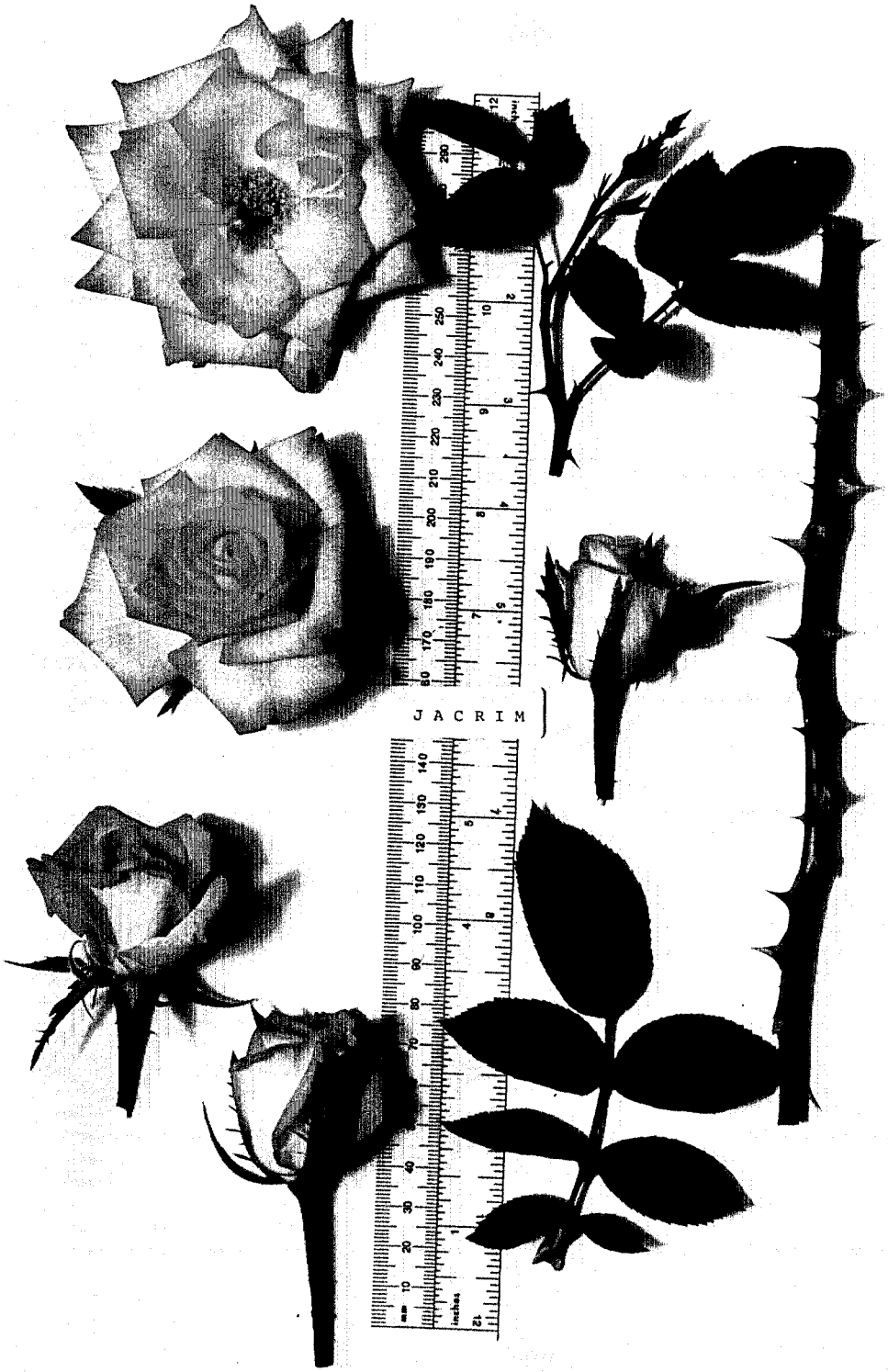
JACRIM